April 16, 1946. B. R. LEACH Plant Pat. 681
AZALEA PLANT
Filed June 8, 1945
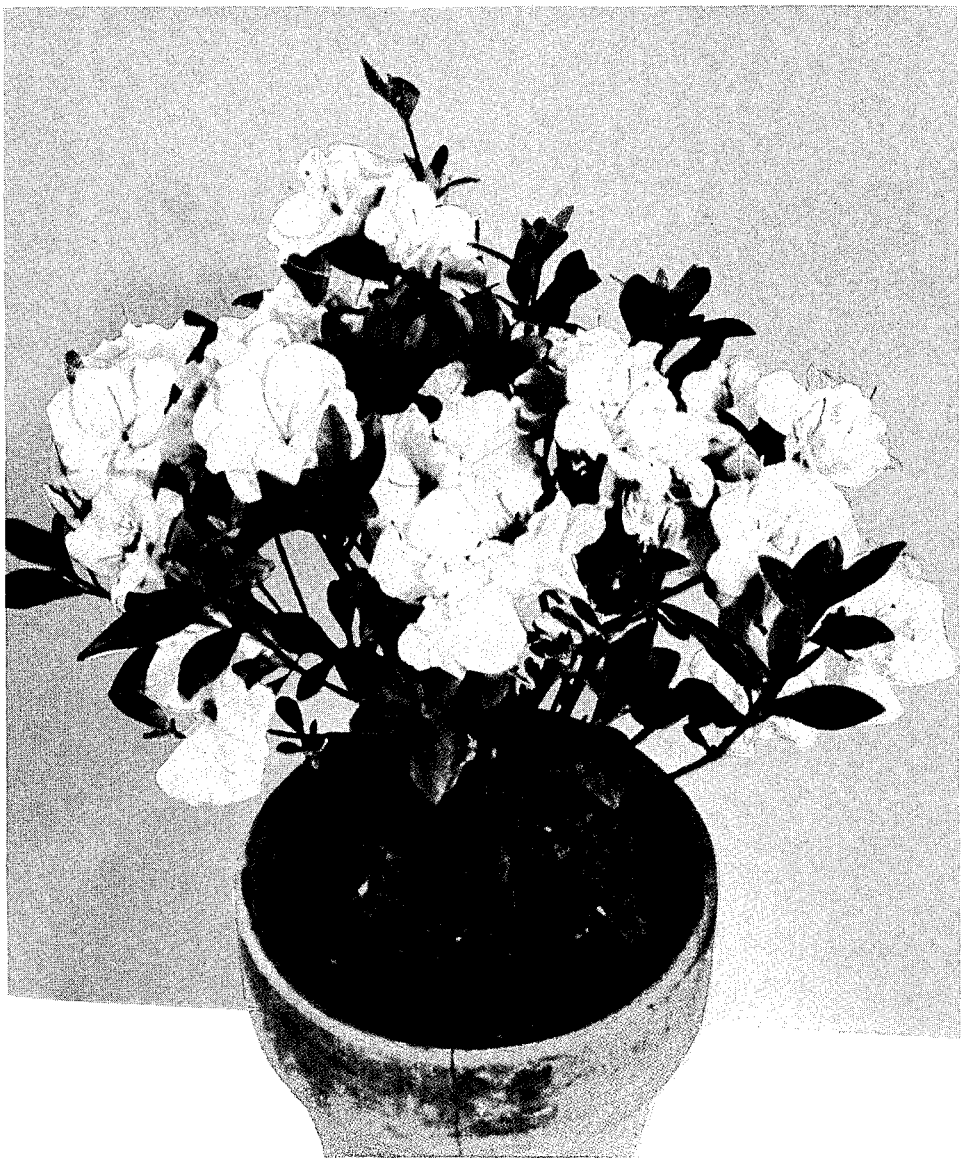
INVENTOR
Benjamin R Leach
By Orville M Kile
Plant Pat. Agt.

Patented Apr. 16, 1946

Plant Pat. 681

UNITED STATES PATENT OFFICE

681

AZALEA PLANT

Benjamin R. Leach, Cinnaminson, N. J.

Application June 8, 1945, Serial No. 598,296

1 Claim. (Cl. 47—60)

My present variety is an improvement in hardy azaleas which are also used for greenhouse forcing. It is a distinct new type of azalea although similar to the semi-double Belgian Indicas in many respects.

The parentage of my new variety is not known. It was discovered by me as a seedling among plants grown from a quantity of seed. I have since developed and propagated the variety, and its characteristics have proved to be permanently fixed.

The accompanying illustration shows in approximately its true colors, a forced plant three years old which had annually been heavily trimmed for cuttings.

Following is a detailed description of the plant and flower, color plate references being to Ridgway's Color Standards and Nomenclature.

*The plant*

Growth: This variety grows more rapidly than the Belgian Indicas, adding 8 to 12 inches of growth each year. It is an early forcer and can readily be brought into bloom for Christmas. It readily produces excellent plants on its own roots and therefore does not need to be grafted.

*Form.*—Slightly spreading; symmetrical.

*Hardiness.*—The variety is exceptionally bud hardy as well as wood hardy, thus making it an excellent outdoor plant even as far north as New York city.

*Stems.*—Woody; sturdy.

Foliage:

*Quantity.*—Sufficient at blooming time to make an interesting background for the flowers. Later more foliage develops.

*Type.*—Semi-evergreen, about half the leaves dropping during the winter months. Because of the partially evergeen nature of the foliage as well as its large size, this is a decorative plant even when not in bloom.

*Color.*—Foliage at the time of bloom is between Cress Green and Dark Cress Green (Plate XXXI). Somewhat lighter new foliage begins to appear at blooming time and develops after the blooms die.

*Shape.*—Broad spatulate.

*Size.*—Large, varying from ½ inch to 1½ inches long and ¼ to ¾ inch wide.

*Arrangement.*—Leaves appear mostly in clusters at the end of relatively long stems.

*The flower*

Size: Diameter 2 to 2¾ inches. Lobes 1¼ to 1½ inches long and ⅞ inch wide.

Form: Flowers are of the hose-in-hose, semi-double formation, consisting of two tubes of five lobes each, one set within the other. The flowers open wide and flat beginning at the point where the tube divides into lobes or petals. The petals in the outer row curve backward slightly. In some of the flowers the petals of the inside row lie flat against the outside row making a formal camelia-like appearance. In other flowers the inside row of petals is frilled and raised in the center in a peony-like appearance covering the center of the flower. The pistil is very long and of darker color than the flower (approximately Rose Red, Plate XII). It adds much to the decorative appearance and remains after the petals have dropped. No stamens are found in this variety.

Borne: Usually in groups of two or three.

Petals:

*Color.*—The color of most of the flowers is a true Deep Rose Pink (Plate XII) upon opening, and this usually lightens somewhat just before the petals drop off

*Texture and aspect.*—Silky.

*Shape.*—Broad, with rounded tip; little or no serration.

*Size.*—Approximately ¾ inch wide.

*Persistence.*—Last a very long time then drop off cleanly leaving pistil.

*Comparison*

My new variety somewhat resembles the average semi-double Belgian Indicas, but with the following principal differences:

1. The flower of my variety is 2 to 2¾ inches in diameter while the Indicas run between 3 and 4 inches in diameter.

2. Petals of flowers of my variety are not so serrated on the edges as the usual Indica.

3. Inside row of petals of my variety often lie flat against the outside row making a formal appearance, as contrasted with the heavily frilled center of the Indica blooms.

4. My variety is extremely bud hardy whereas Indicas are not rated as hardy.

5. My variety is more easily forced for early blooming.

Having thus disclosed my invention, I claim:

The new and useful variety of azalea plant substantially as herein shown and described, characterized particularly by its extreme hardiness; its ease of reproduction on its own roots; its large semi-evergreen foliage; its early forcing quality; its Deep Rose Pink semi-double flowers of medium size, frequently formal arrangement and smooth unserrated petals.

BENJAMIN R. LEACH.